US012268245B2

(12) United States Patent
Moloney et al.

(10) Patent No.: US 12,268,245 B2
(45) Date of Patent: *Apr. 8, 2025

(54) AEROSOL DELIVERY DEVICE, AN ARTICLE FOR USE THEREWITH AND A METHOD OF IDENTIFYING AN ARTICLE

(71) Applicant: NICOVENTURES TRADING LIMITED, London (GB)

(72) Inventors: Patrick Moloney, London (GB); Anton Korus, London (GB); Justin Han Yang Chan, London (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,535

(22) Filed: Apr. 4, 2023

(65) Prior Publication Data

US 2023/0232906 A1 Jul. 27, 2023

Related U.S. Application Data

(63) Continuation of application No. 15/733,694, filed as application No. PCT/EP2019/057781 on Mar. 27, 2019, now Pat. No. 11,707,093.

(30) Foreign Application Priority Data

Mar. 29, 2018 (GB) ........................... 1805257

(51) Int. Cl.
*A24D 1/20* (2020.01)
*A24F 40/50* (2020.01)
(Continued)

(52) U.S. Cl.
CPC ................ *A24F 40/50* (2020.01); *A24D 1/20* (2020.01); *A24F 40/53* (2020.01); *A61M 21/00* (2013.01);
(Continued)

(58) Field of Classification Search
CPC ........... A24D 1/20; A24F 40/53; A24F 40/20; G06K 7/087; G06K 7/10366; G06K 7/12; G06K 7/1404
See application file for complete search history.

(56) References Cited

U.S. PATENT DOCUMENTS 8,155,717 B1 * 4/2012 Watson ................... H04M 1/18
455/90.3
2009/0321623 A1 12/2009 Ross et al.
(Continued)

FOREIGN PATENT DOCUMENTS

CN 107183784 A 9/2017
EA 029918 B1 5/2018
(Continued)

OTHER PUBLICATIONS

"Examination Report received for Australian Patent Application No. 2019241462, mailed on Dec. 15, 2021", 7 Pages.
(Continued)

*Primary Examiner* — Jamara A Franklin
(74) *Attorney, Agent, or Firm* — BURR & FORMAN LLP

(57) ABSTRACT

An article including an aerosolizable material; and a signal altering component, wherein the signal altering component is configured to alter a first signal transmitted at least partially through the article into a second signal indicative of article data.

4 Claims, 5 Drawing Sheets

(51) Int. Cl.
  *A24F 40/53*  (2020.01)
  *A61M 21/00*  (2006.01)
  *G06K 7/08*  (2006.01)
  *G06K 7/10*  (2006.01)
  *G06K 7/12*  (2006.01)
  *G06K 7/14*  (2006.01)
  *A24F 40/20*  (2020.01)

(52) U.S. Cl.
  CPC ......... *G06K 7/087* (2013.01); *G06K 7/10366* (2013.01); *G06K 7/12* (2013.01); *G06K 7/1404* (2013.01); *A24F 40/20* (2020.01); *A61M 2021/0016* (2013.01)

(56) References Cited

U.S. PATENT DOCUMENTS

| | | | |
|---|---|---|---|
| 2013/0221097 A1 | 8/2013 | Day et al. | |
| 2016/0302488 A1* | 10/2016 | Fernando | H02J 7/0042 |
| 2017/0071255 A1 | 3/2017 | Revell | |
| 2017/0156399 A1 | 6/2017 | Freeman et al. | |
| 2017/0181223 A1 | 6/2017 | Sur et al. | |
| 2017/0340009 A1 | 11/2017 | Hon | |
| 2018/0160734 A1 | 6/2018 | Batista et al. | |

FOREIGN PATENT DOCUMENTS

| | | | |
|---|---|---|---|
| EP | 2399636 A1 | 12/2011 | |
| GB | 2087197 A | 5/1982 | |
| GB | 2533652 A | 6/2016 | |
| JP | S57134789 A | 8/1982 | |
| JP | 2016526873 A | 9/2016 | |
| JP | 2017501682 A | 1/2017 | |
| JP | 2017510270 A | 4/2017 | |
| JP | 2017533732 A | 11/2017 | |
| JP | 2018532392 A | 11/2018 | |
| JP | 2018536841 A | 12/2018 | |
| JP | 2019515764 A | 6/2019 | |
| JP | 2019528708 A | 10/2019 | |
| RU | 2509516 C2 | 3/2014 | |
| RU | 2595593 C2 | 8/2016 | |
| RU | 2606942 C2 | 1/2017 | |
| RU | 2654619 C1 | 5/2018 | |
| RU | 2655596 C2 | 5/2018 | |
| RU | 2674494 C2 | 12/2018 | |
| RU | 2678912 C1 | 2/2019 | |
| WO | 2010073122 A1 | 7/2010 | |
| WO | 2011160788 A1 | 12/2011 | |
| WO | 2012022771 A2 | 2/2012 | |
| WO | 2013060781 A1 | 5/2013 | |
| WO | 2014061082 A1 | 4/2014 | |
| WO | 2015039849 A1 | 3/2015 | |
| WO | 2015140312 A1 | 9/2015 | |
| WO | 2016075436 A1 | 5/2016 | |
| WO | 2017019428 A1 | 2/2017 | |
| WO | 2017045897 A1 | 3/2017 | |
| WO | 2017045899 A1 | 3/2017 | |
| WO | 2017060328 A1 | 4/2017 | |
| WO | 2017137138 A1 | 8/2017 | |
| WO | 2017192767 A1 | 11/2017 | |
| WO | 2018046192 A1 | 3/2018 | |
| WO | 2019130128 A1 | 7/2019 | |

OTHER PUBLICATIONS

"International Preliminary Report on Patentability received for PCT Patent Application No. PCT/EP2019/057781, mailed on Sep. 29, 2020", 9 Pages.

"International Search Report and Written Opinion received for PCT Patent Application No. PCT/EP2019/057781, mailed on Jul. 11, 2019", 11 Pages.

"Notice of Reasons for Refusal received for Japanese Patent Application No. 2020-551838, mailed on Dec. 7, 2021", 10 Pages.

"Office Action received for Russian Patent Application No. 2020131959, mailed on Oct. 22, 2021", 8 Pages.

"Search Report received for Japanese Patent Application No. 2020-551838, mailed on Nov. 30, 2021", 38 pages (22 pages of English Translation and 16 pages of Official Copy).

"Search Report received for Russian Patent Application No. 2020131959, mailed on May 28, 2021", 2 Pages.

Communication pursuant to Article 94(3) EPC issued in European Application No. 19718577.0 on May 17, 2024, all enclosed pages cited.

* cited by examiner

AEROSOL DELIVERY DEVICE, AN ARTICLE FOR USE THEREWITH AND A METHOD OF IDENTIFYING AN ARTICLE

PRIORITY CLAIM

The present application is a Continuation Application of U.S. application Ser. No. 15/733,694, filed on Sep. 29, 2020, which is a National Phase entry of PCT Application No. PCT/EP2019/057781, filed Mar. 27, 2019, which claims priority from GB Patent Application No. 1805257.1, filed Mar. 29, 2018, each of which is hereby fully incorporated herein by reference.

TECHNICAL FIELD

The present disclosure relates to an aerosol delivery device, an article for use therewith, and a system and a method of identifying an article.

BACKGROUND

Articles such as cigarettes, cigars and the like burn tobacco during use to create tobacco smoke. Attempts have been made to provide alternatives to these articles, which burn tobacco, by creating products that release compounds without burning. Examples of such products are so-called heat-not-burn products, also known as tobacco heating products or tobacco heating devices, which release compounds by heating, but not burning, the material. The material may be, for example, tobacco or other non-tobacco products or a combination, such as a blended mix, which may or may not contain nicotine.

SUMMARY

In accordance with some examples described herein, there is provided an aerosol delivery device comprising: a chamber for receiving an article comprising an aerosolizable material for delivery by the aerosol delivery device, a transmitter, a receiver spaced apart from the transmitter, and a processor, wherein the processor is configured to: cause the transmitter to transmit a first signal to the receiver at least partially through an article in the chamber in use, so that the receiver receives a second signal, wherein the second signal is the first signal altered by interaction with a signal altering component of the article, and determine article data from the second signal.

In accordance with some examples described herein, there is provided an article comprising: an aerosolizable material; and a signal altering component; wherein the signal altering component is configured to alter a first signal transmitted at least partially through the article into a second signal indicative of article data.

In accordance with some examples described herein, there is provided a system comprising: an aerosol delivery device as describe above and an article as described above.

In accordance with some examples described herein, there is provided a method of identifying an article in an aerosol delivery device, the method comprising: transmitting a first signal at least partially through an article from a transmitter to a receiver spaced from the transmitter, receiving a second signal at the receiver, wherein the second signal is the first signal altered by interaction with a signal altering component of the article, and determining article data from the second signal.

In an example, an aerosol delivery device may comprise: a chamber into which a consumable can be inserted, a field generator, a field receiver spaced from the field generator, and a processor, wherein the field generator is configured to generate a field across a portion of the receptacle to the field receiver, and the processor is configured to: identify an alteration in the field at the field receptor in response to insertion of a consumable into the receptacle, the consumable including a field altering component; and determine which one of a plurality of field altering components the consumable includes based on the identified alteration.

Further features and advantages of the disclosure will become apparent from the following description of embodiments of the disclosure, given by way of example only, which is made with reference to the accompanying drawings.

DETAILED DESCRIPTION

Figure 1:
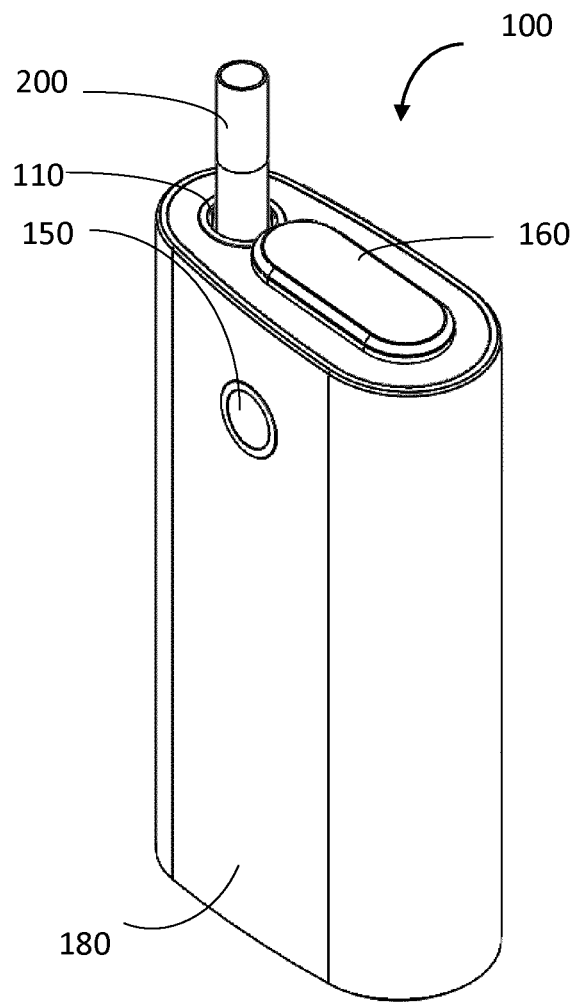
FIG. 1 shows a schematic perspective view of an aerosol delivery device according to an example.

Referring to FIG. 1, a schematic perspective view of an example aerosol delivery device 100 is shown. The aerosol delivery device 100 is arranged to volatilize at least one component of aerosolizable material.

The aerosol delivery device 100 has a housing 180 and a receptacle 110, such as a chamber, cavity, or holder.

The receptacle 110 receives a consumable 200, such as an article comprising an aerosol generating material (aerosolizable material) from which an aerosol may be generated, e.g., through the application of heat to the aerosolizable material. The consumable 200 may be an article comprising an aerosol generating material for delivery by the aerosol delivery device. The consumable 200 may be a tobacco heating product (THP) article.

As used herein, the term "aerosol generating material" and "aerosolizable material" refer to material that provides volatilized components upon the application of energy (e.g., such as heating) in the form of an aerosol. In some embodiments, the aerosol generating material may comprise a tobacco component, wherein tobacco component is any material comprising tobacco or derivatives thereof. The tobacco component may comprise one or more of ground tobacco, tobacco fiber, cut tobacco, extruded tobacco, tobacco stem, reconstituted tobacco and/or tobacco extract. Other types of aerosolizable may include leaf material, herbal material or organoleptic substances as used in aromatherapy and the like. In some embodiments, the aerosol-generating substrate may comprise a tobacco substitute.

The aerosol delivery device 100 in this example also has a cover 160. The cover 160 is moveable to cover the receptacle 110 when an article, such as consumable 200, is not present within receptacle 110. In other examples, the aerosol delivery device 100 may not include a cover 160.

The aerosol delivery device 100 also has a power button 150. In use, when the aerosol delivery device 100 is switched on using the power button 150, power from a power source (such as a battery within the device 100) is supplied to various components of the device, e.g., in response to pressing the power button 150, power may flow to a heater such that the consumable 200 is heated and a flow of aerosol is generated from the consumable 200.

Figure 2:
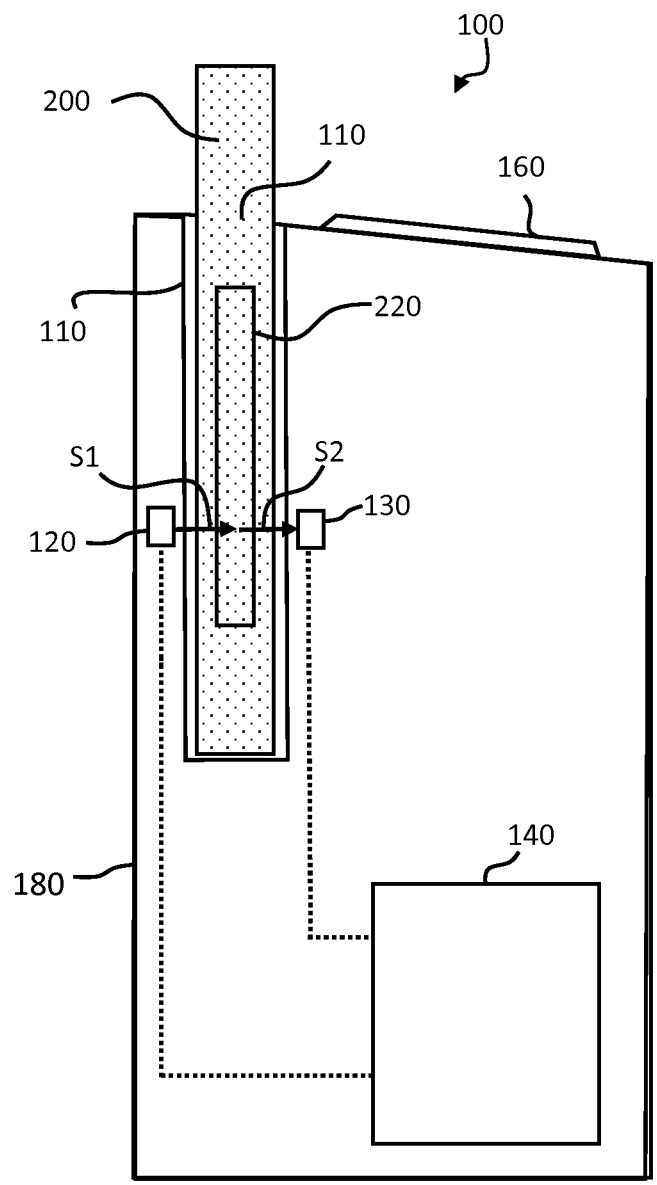
FIG. 2 shows a schematic internal side view of the aerosol delivery device of FIG. 1.

As illustrated in FIG. 2, an example of an internal side view of the aerosol delivery device 100 of FIG. 1 is shown. The receptacle 110 of the aerosol delivery device 100 contains a consumable 200. The consumable 200 has a signal altering component 220.

The signal altering component 220 of the consumable 200 may be at least one of: a shield; a susceptor; a conductor; a diffraction grating/a refractor, a signal reflector, and a polarizer. The signal altering component 220 may alter at least one of: signal strength (or intensity); signal polarization; signal frequency; signal wavelength; and signal direction. It should be appreciated that how the signal altering component 220 alters the signal (discussed below) will depend upon the specific signal altering component 220 present in the consumable 200.

The aerosol delivery device 100 of the example has a transmitter 120 and a receiver 130 spaced apart from the transmitter 120. The aerosol delivery device 100 also has device circuitry 140 coupled to the transmitter 120 and the receiver 130. The device circuitry 140 may comprise a processor.

The terms "transmitter" and "receiver" are used to refer to components which can transmit and receive a signal in the general sense that a signal from the transmitter can be detected by the receiver. The transmitter 120 may transmit at least one of the following: an electric field, a magnetic field, a radio frequency signal, an Infra-Red signal, a visible light signal, an Ultra-Violet signal, and an acoustic or sonic signal. For example, the transmitter 120 may be an LED that transmits visible light, Infra-Red light and/or Ultra-Violet light, or a radio frequency transmitter. In other examples, the transmitter 120 may be a field generator comprising a charge carrying wire (to generate a magnetic field) or a capacitor plate (to generate an electric field). In other examples the transmitter 120 may be a transducer, for example a transducer for producing sound waves. The sound may be audible to humans, for example having a frequency below about 20 kHz, or may be ultrasonic, such as having a frequency above about 20 kHz. It should be appreciated that the type of transmitter 120 and receiver 130 are selected so as to be receptive to changes in the signal as affected by the chosen signal altering component 220, or by one or more signal altering components 220 present in a single, or over several, consumables 200.

In use, if the transmitter 120 generates an electric field or a magnetic field, a corresponding signal (a first signal) is generated in the receiver. This first signal is a signal generated in the absence of a signal altering component 220. The generated signal can be measured, for example by measuring a current flowing or the overall capacitance between the transmitter 120 and the receiver 130. The coupling of the electric field or magnetic field to the receiver 130 is changed when a consumable 200 with a signal altering component 220 is positioned between the transmitter 120 and receiver 130, in a receptacle 100 of the aerosol delivery device 100.

In one example, the dielectric constant between the plates of a capacitor formed by the transmitter 120 and receiver 130 is changed by the signal altering component 220, and the particular capacitance, or change in capacitance can be detected.

In another example the inductive coupling between the transmitter 120 and receiver 130 is altered by the signal altering component, such as by changing the magnetic permeability of the medium between the elements. The change in the coupling causes a change in the current induced in the receiver 130 (a second signal) and this can be used to determine consumable data.

Properties relating to the receiver 130, such as a current flowing through the receiver or a property of the received signal, may be measured for the second signal only (i.e., the first signal as altered by the signal altering component 220), or may be measured both when the receiver receives a first signal (i.e., when no consumable is present in the chamber) and when the receiver receives the second signal. If both the first signal and the second signal are measured by the receiver 130, the alteration in the properties relating to the receiver may be determined and associated consumable data derived from the alteration. A look up table may be stored in a memory and used to determine consumable data associated with the second signal or with the determined alteration. In other implementations, a processor in the device 100 may be configured to perform a similar comparison using the drive signal for the transmitter 120 (which may be the same or at least corresponds to the first signal) and the received signal (i.e., the second signal).

The receiver 130 may be at least one of an electric field receptor, a magnetic field receptor, such as a susceptor, a signal receptor (such as an RF receptor) and a sonic receptor. For example, the receiver may be at least one of a capacitor plate, a wire, such as a non-charge carrying wire, an antenna, and a microphone.

The dotted lines of FIG. 2 denote a communicative coupling between the transmitter 120 and the device circuitry 140 and between the receiver 130 and the device circuitry 140. The coupling may be wired or wireless. The device circuitry 140 is discussed in more detail in relation to FIG. 3 below.

As depicted in FIG. 2, in this example the transmitter 120 is located on one side of the receptacle 110 and the receiver 130 is on an opposite side of the receptacle 110. The transmitter 120 and receiver 130 are directly opposite one another. In other examples, the transmitter and receiver can be in different relative positions, but still spaced from each other. For example, the transmitter and receiver may be offset from one another along an insertion axis of the consumable, while remaining broadly on opposite sides of the receptacle 110. The transmitter 120 and receiver 130 may be positioned so at least a portion of the receptacle is located between them, for example they may be radially offset from one another, such as a radial offset around an insertion axis of the consumable. A radial offset may mean that a first line normal to an insertion axis and passing through the transmitter 120, and a second line normal to the insertion axis and passing through the receiver form an angle about the insertion axis which is less than 180°.

In use, the transmitter 120 is configured to transmit a first signal, S1, at least partially through the consumable 200 in the receptacle 110 to the receiver 130. The receiver 130 is configured to receive a second signal, S2. The second signal S2 is the first signal S1 altered by interaction with the signal altering component 220 of the consumable 200.

The signal altering component 220 alters the first signal S1 in a predetermined manner specific to the signal altering component 220. The alteration may be a modification of a physical characteristic of the first signal. For example, the alteration may be a change of at least one of signal strength/intensity, signal frequency, signal wavelength, signal polarization, and signal direction. In some examples, the alteration may be dependent on the type/strength of signal S1. Across the whole system, there may be a plurality of signal altering components, each configured in a different, predetermined way, such that a particular one of the plurality of signal altering components can be identified based on the second signal. For instance, different consumables 200 may be provided with different signal altering components such that the different consumables 200 can be distinguished from one another on the basis of the alteration to the first signal. This may be implemented when, e.g., the different consumables comprise different aerosolizable material (e.g., providing different flavors). In this way, the device 100 is configured to identify the consumable inserted into the receptacle, and the device 100 may alter an aspect of its operation (such as a heating profile) on the basis of the identified consumable. Example signal altering components will now be described.

In a first example, the signal altering component 220 may comprise a polarizer, such as a linear polarizer, that changes the polarization of signal S1 to a certain polarization, e.g., horizontally polarized, so that signal S2 is, in this example, horizontally polarized. Signal S1 may be generated at a single polarization, or at multiple polarizations, and the signal altering component 220 may be configured to change the polarisation(s). A plurality of signal altering components may each change a polarization in a different way, for example vertical or horizontal polarization. The specific type of polarizer used will be dependent upon the wavelength of the signal S1. The wavelength of signal S1 may be chosen in correspondence with the materials used in the consumable 200 such that the signal S1 is able to penetrate through at least a part of the consumable 200 but such that the signal S1 interacts with the polarizer.

In a second example, the signal altering component 220 may comprise a component that alters the direction of at least a part of the signal S1. For example, the signal altering component may be a diffraction grating, or a component that causes refraction of the signal S1. A diffraction grating may change the direction of the first signal S1 by a predetermined amount, or to change the directions of different components of the first signal S1, which is detected by the receiver 130. The change of direction may be measured by an increase or a decrease in the signal power of the second signal S2 detected at the receiver 130 positioned at a known position relative to the transmitter 120. The receiver 130 may also comprise a sensor array, such as an imaging sensor, which is configured to sense a diffraction pattern resulting from the signal passing through the diffraction grating. The diffraction pattern can be measured by sensing the change in signal intensity over an area/plane (e.g., the area/plane of the sense surface of the receiver 130). A plurality of signal altering components may each produce a different diffraction pattern, and/or change the direction of a signal by a different amount. The diffraction grating may have a regular or an irregular spacing (or combinations thereof) to create certain intensity patterns. In the case of a signal altering component that causes refraction of the signal S1, the receiver 130 may be adapted to sense a position at which the signal S2 is received on the receiver 130 (again, the receiver may be a sensor array) or alternatively one or more sensors of the sense array comprising the receiver 130 may be positioned relative to the transmitter 120 by an expected amount of refraction for each of the different signal altering components 220.

In a third example, when the transmitter 120 transmits an electric field, the signal altering component 220 may comprise a dielectric material that changes the permittivity between the transmitter 120 (transmitting an electric field) and the receiver 130. In one example, the dielectric material changes the capacitance between the transmitter and receiver. The dielectric material may, in this implementation, include the aerosolizable material and/or other materials of the consumable 200. In other examples, the dielectric material is a component distinct from the aerosolizable material and/or other materials of the consumable. A plurality of signal altering components may each result in a different effective capacitance between the transmitter and the receiver, through the use of different materials and/or dimensions of material In a fourth example, the transmitter 120 may be an inductor or similar component configured to generate a magnetic field, and the signal altering component may comprise a ferrite or the like, to alter the relative permeability between the transmitter 120 and the receiver 130. A plurality of signal altering components may each result in different levels of inductive coupling between the transmitter and receiver, through the use of different ferrite materials and/or dimensions.

In a fifth example, the signal altering component 220 may comprise an attenuator, such as a shield, whereby the transparency of the signal altering component 220 to the first signal S1 is predetermined. The attenuator may be a radio frequency attenuator that attenuates the first signal S1 (which in this example is a radio frequency signal) by a predetermined amount. For example, the signal altering component 220 may reduce the signal strength of the first signal S1 by one of the following: 5 dB, 10 dB, and 20 dB. In another example, the attenuator may attenuate a signal from an LED (transmitter) by a defined amount, such as reducing the intensity of signal by 25%, 50% or 75%. It should be appreciated that these numerical values are given as examples only and different numerical values may be applicable in other implementations. A plurality of signal altering components may each result in different levels of attenuation, for example by the material and dimensions of the signal altering component.

In a sixth example, the signal altering component 220 may be a fluorescent material. In one example, the fluorescent material may fluoresce at a lower frequency and/or lower energy than the stimulus, such as incident light. In another example, the fluorescent material may fluoresce at a higher frequency than the stimulus. In one example, the fluorescent material may be such that it fluoresces at a visible wavelength in response to incident ultra violet light. Accordingly, in this example the signal altering component 220 receives the first signal S1 as ultra violet light and emits the second signal S2 as visible light, so the second signal S2 has a different wavelength (and frequency) compared to the first signal S1. A plurality of signal altering components may each result in different fluorescent responses through material choices of the signal altering component, for example changing a wavelength of excitation or a wavelength of fluorescence. An example of a fluorescent material is pyranine. Any other suitable material exhibiting fluorescence may be used. In some examples, the fluorescent material is a food additive, which may be beneficial for the safety of the user. Example food additives which exhibit fluorescence include quinine and B2 riboflavin.

It should be appreciated that the above provides a non-exhaustive list of forms that the signal altering component 220 may take, and the signal altering component 220 may be arranged to alter any other measurable/detectable parameter of a signal that passes through at least a portion of the consumable 200. For instance, the signal altering component 220 may be chosen to alter the phase of the signal S1 by a predetermined amount by selecting an appropriate signal altering component 220 for the signal S1.

The signal altering component 220 may comprise at least two signal altering elements as described above that alter a plurality of physical characteristics of signal S1. This may allow a greater number of unique identifying characteristics. For example, is a first signal altering component allows distinguishing between 4 values of first signal property, and a second signal altering component allows distinguishing between another 4 values of second signal property, in total 16 unique combinations can be created. The number of values may be different from this example, for example 32 values for each property would allow 1024 unique combinations. Combining properties in this way may allow for a greater number of combinations with reduced transmitter and receiver cost; although two properties are measured in the second signal, the overall cost may be lower as a lower sensitivity of detection is required for each property than achieving the same number with only a single property.

As mentioned above, the alteration to the first signal S1 by the signal altering component 220 is a predetermined alteration specific to the signal altering component 220. In addition, the device circuitry 140 is configured to determine article data, such as consumable data, from the second signal S2 received by the receiver 130. The specific alteration to the first signal by the signal altering component can be associated with consumable data, or the specific second signal itself can be associated with consumable data.

The consumable data is at least one of: a type of consumable (for example the type of aerosolizable material such as a gel, a fluid, a liquid, or a solid), a flavor or flavorant of the consumable (or of the aerosol able to be generated from the consumable), a strength of the active (such as nicotine) released from the aerosolizable material, an identifier of the consumable (for example a batch identifier, or an individual identifier), and a source of the consumable (for example one of more of a manufacturing facility, an assembly facility, a country, a date of manufacture, and a time of manufacture).

As an example, a signal alteration of an increase of signal wavelength from ultra violet to visible light may be associated with a specific signal altering component. In this example, the specific signal altering component may be associated with consumable data that identifies that the consumable is a gel type and is part of a particular batch sourced from a particular manufacturing facility.

As a further example, a signal alteration of an increase in signal strength of 10 dB at a radially offset receiver may indirectly indicate a change in signal direction away from the normal. This may be associated with a different specific signal altering component and linked to a particular consumable article.

The device 100 may determine the presence of the consumable 200 within the receptacle 110. The presence of the consumable 200 may be detected using the transmitter 120 and the receiver 130. The presence of an item in the receptacle will alter the received signal in some way. However, only consumables with known, predetermined signal altering components will alter the signal in a predetermined way. Thus, transmitter and receiver may operate in a first mode to detect a presence of a consumable and a second mode in which a specific received signal is interpreted to identify the signal altering component. Alternatively, the presence of the consumable 200 may be detected by an independent presence sensor, such as a capacitive sensor located adjacent the receptacle 110.

Figure 3:
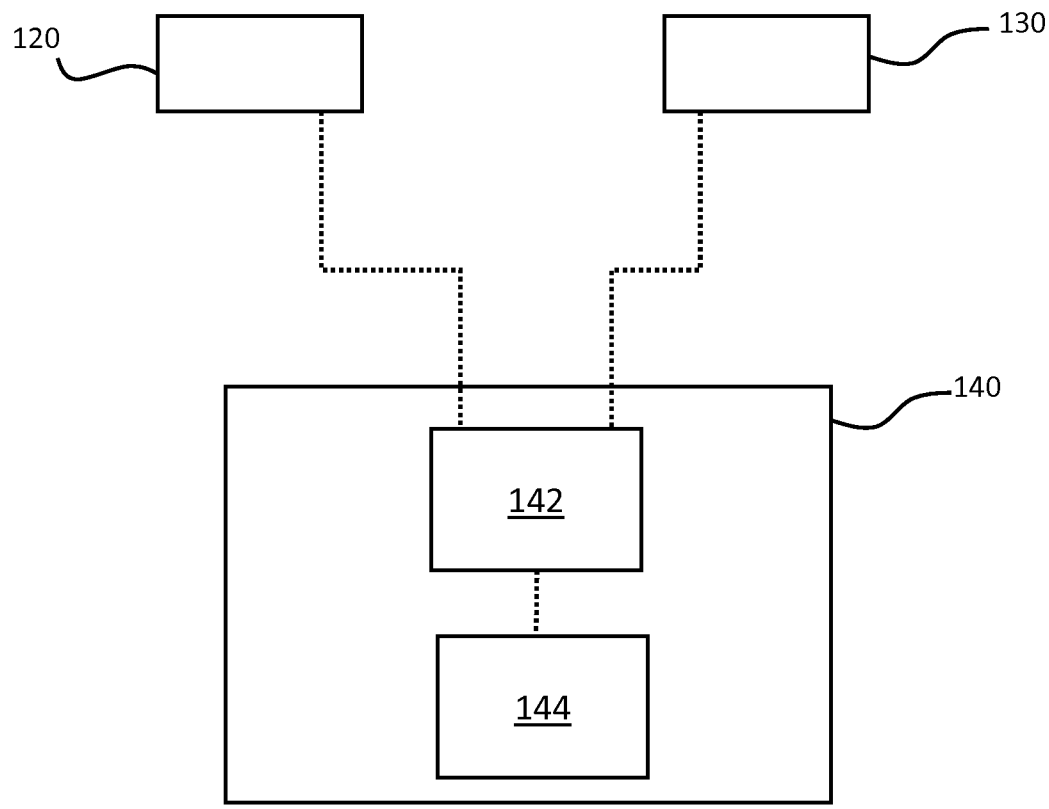
FIG. 3 shows a functional block diagram of an aerosol delivery device according to an example.

Referring now to FIG. 3, an example functional block diagram of device circuitry of an aerosol delivery device, such as device circuitry 140 of the aerosol delivery device 100 of FIGS. 1 and 2, is shown. As in FIG. 2, the device circuitry 140 is communicatively coupled to the transmitter 120 and the receiver 130. The dotted lines between the components indicate that the coupling may be wired or wireless.

In this example, the device circuitry 140 contains a processor 142, a memory 144, and a power source (not shown).

The processor 142 is configured to cause the transmitter 120 to transmit a first signal, S1, at least partially through the consumable 200 in the receptacle 110, to the receiver 130 so that the receiver 130 receives a second signal, S2. As explained in relation to FIG. 2, the second signal S2 is the first signal S1 altered by interaction with the signal altering component 220 of the consumable 200. The processor 142 is configured to determine consumable data from the second signal S2. In an example, the receiver 130 may send a signal representative of the second signal S2 to the processor 142.

As discussed in relation to FIG. 2, the alteration to the first signal S1 is specific to the signal altering component 220. Different signal altering components alter the first signal in different ways so identification of a signal altering component (and associated consumable data) can be based on a determined alteration to the first signal.

The memory 144 stores consumable data for a plurality of consumables and corresponding signal altering data for a plurality of signal altering components. In other implementations, the device 100 may be coupled to a communication network and the determination of the signal altering component may be performed remote from the device 100. Certain signal altering components may be assigned to certain groups of consumables or individual consumables. Identification of a signal altering component of a consumable, through identification of a signal alteration made to the first signal, or directly from the second signal, enables determination of consumable data of the consumable by looking up a predetermined signal alteration, or second signal, in the memory 144.

For example, signal altering data stored by the memory 144 may be predetermined signal alterations produced by different signal alternating component configurations. The predetermined signal alterations may contain alterations stored in the memory 144 as a factory setting during manufacture. The memory 144 may also store reference signal data representative of a received signal when the consumable 220 with the signal altering component 220 is not present within the receptacle. In one example, the reference signal data may correspond to signal data associated with the first signal S1.

In use, to determine consumable data from the second signal, S2, the processor 142 may compare the first signal S1 to the second signal S2 and determine the alteration of the first signal S1 by the signal altering component 220. As an alternative, the processor 142 may compare the second signal directly to a stored reference signal to determine the alteration by the signal altering component. The stored reference signal may be a signal received by the receiver 130 when the consumable 220 with the signal altering component is not present in the receptacle of the delivery device 100, or may be (or be based on) the drive signal for generating the first signal S1.

The processor 142 compares the determined alteration to a plurality of predetermined alterations stored by the memory 144. For example, the processor 142 may use a look-up table stored in the memory 144.

When the processor 142 identifies a match between the determined alteration and one of the plurality of predetermined alterations, the processor 142 determines the consumable data based on the match. For example, if the determined alteration is an attenuation of signal power of 5 dB, in use, the processor 142 compares the determined alteration of 5 dB to a plurality of predetermined alterations, such as, 5 dB, 10 dB, and 12 dB. In this example, the plurality of predetermined alterations contains 5 dB as a predetermined alteration, so the processor identifies a match and determines consumable data associated with the predetermined alteration of 5 dB.

The second signal may comprise an identifier of the signal altering component 220 and the memory 144 may store predetermined identifiers for different signal altering components and corresponding consumable data. If a match is identified by the processor between the identifier of the second signal and one of the plurality of predetermined identifiers, consumable data associated with the matched predetermined identifier can be determined.

Figure 4:
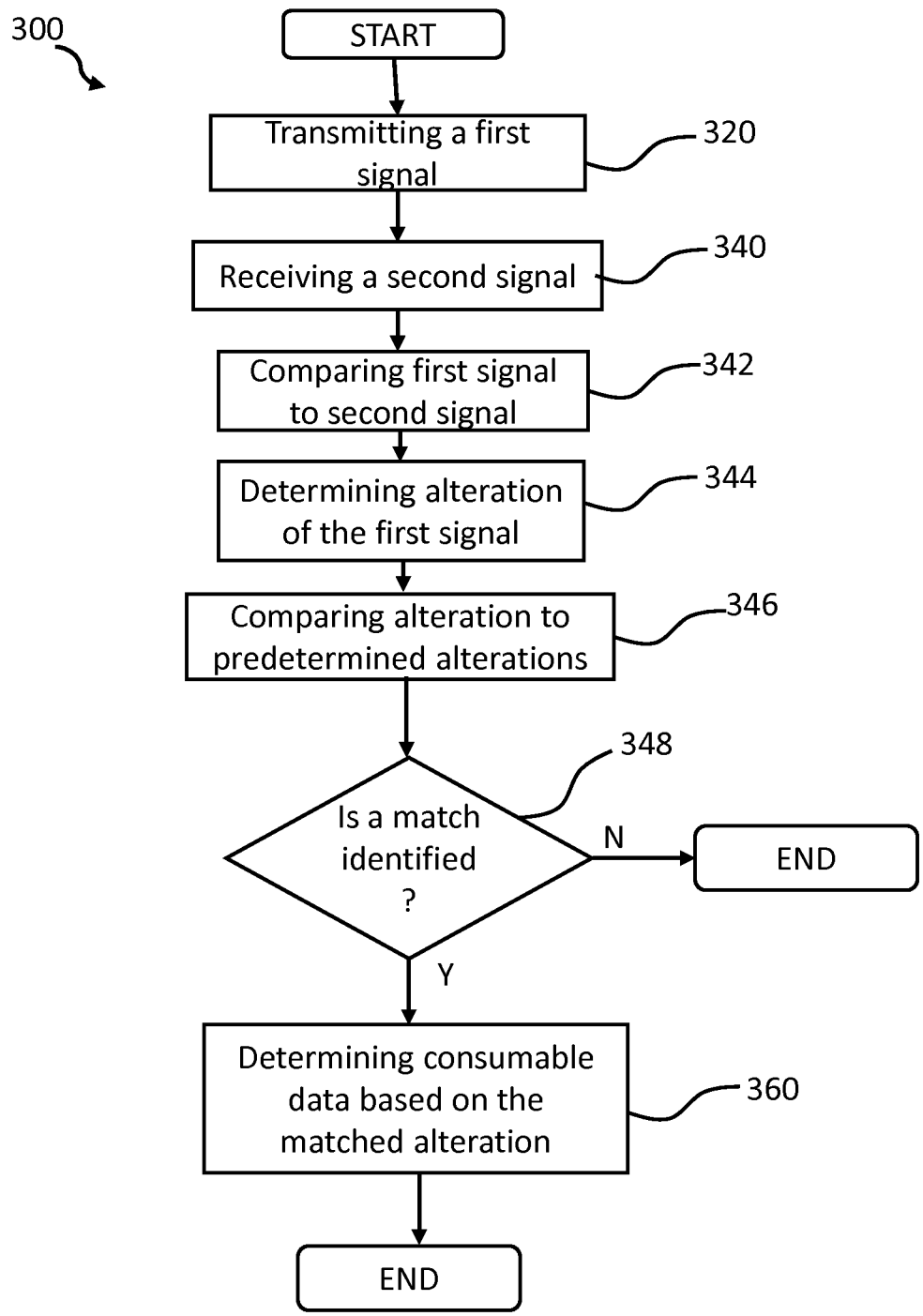
FIG. 4 shows a flow chart of a method of identifying an article of an aerosol delivery device according to an example.

Referring now to FIG. 4, a flow chart of an example method 300 of identifying a consumable, such as consumable 200, in an aerosol delivery device is shown.

The method 300 comprises a first block 320 where a first signal S1 is transmitted at least partially through a consumable 200 from a transmitter 120 to a receiver 130 spaced from the transmitter 120, where the consumable 200 has a signal altering component 220.

After transmitting the first signal S1, the method 300 moves on to block 340, where a second signal S2 is received at the receiver 130. The second signal S2 is the first signal S1 altered by interaction with the signal altering component 220 of the consumable 200.

Next, the method 300 proceeds to block 342, where the first signal S1 is compared to the second signal S2. Following the comparison, at block 344, the alteration applied to the first signal S1 is determined.

After determining the alteration, the method 300 moves on to block 346, where the determined alteration is compared to a plurality of predetermined alterations. The plurality of predetermined alterations is stored in the memory 144 of the device circuitry 140. The comparison at block 346 may compare one or more of signal strength, signal polarization, signal frequency, signal wavelength, and signal direction of the determined alteration to signal strength, signal polarization, signal frequency, signal wavelength, and signal direction of the plurality of predetermined alterations.

Next, at block 348 a query is made as to whether a match can be identified between the determined alteration and one of the plurality of predetermined alterations. If no match is found, the method 300 ends, as shown by the no (N) branch. In some embodiments, if no match is found a feedback signal may be generated to notify a user of the aerosol delivery device 100 that the consumable 200 is not recognized. This may help to draw a user's attention to an incorrect or counterfeit consumable, for example. The feedback signal could be a visual signal, an audible signal or a haptic signal, for example.

On the other hand, if a match is found, method 300 moves on to block 360, where consumable data is determined based on the matched alteration, as shown by the yes (Y) branch. The consumable data is stored in the memory 144 of the device circuitry 140.

The alteration of the first signal S1 by the signal altering component 220 to generate a second signal S2 is specific to the signal altering component 220 of the consumable 200. In this way, identification of the alteration to the first signal S1 by comparing the first signal S1 and the second signal S2, and subsequent matching of the identified alteration to a predetermined alteration enables identification of the signal altering component 220 and subsequently, determination of consumable data of the consumable 200.

In some embodiments, if a match is found a feedback signal may be generated to notify a user of the aerosol delivery device 100 that the consumable 200 is recognized. The signal could be a visual signal, an audible signal or a haptic signal.

Figure 5:
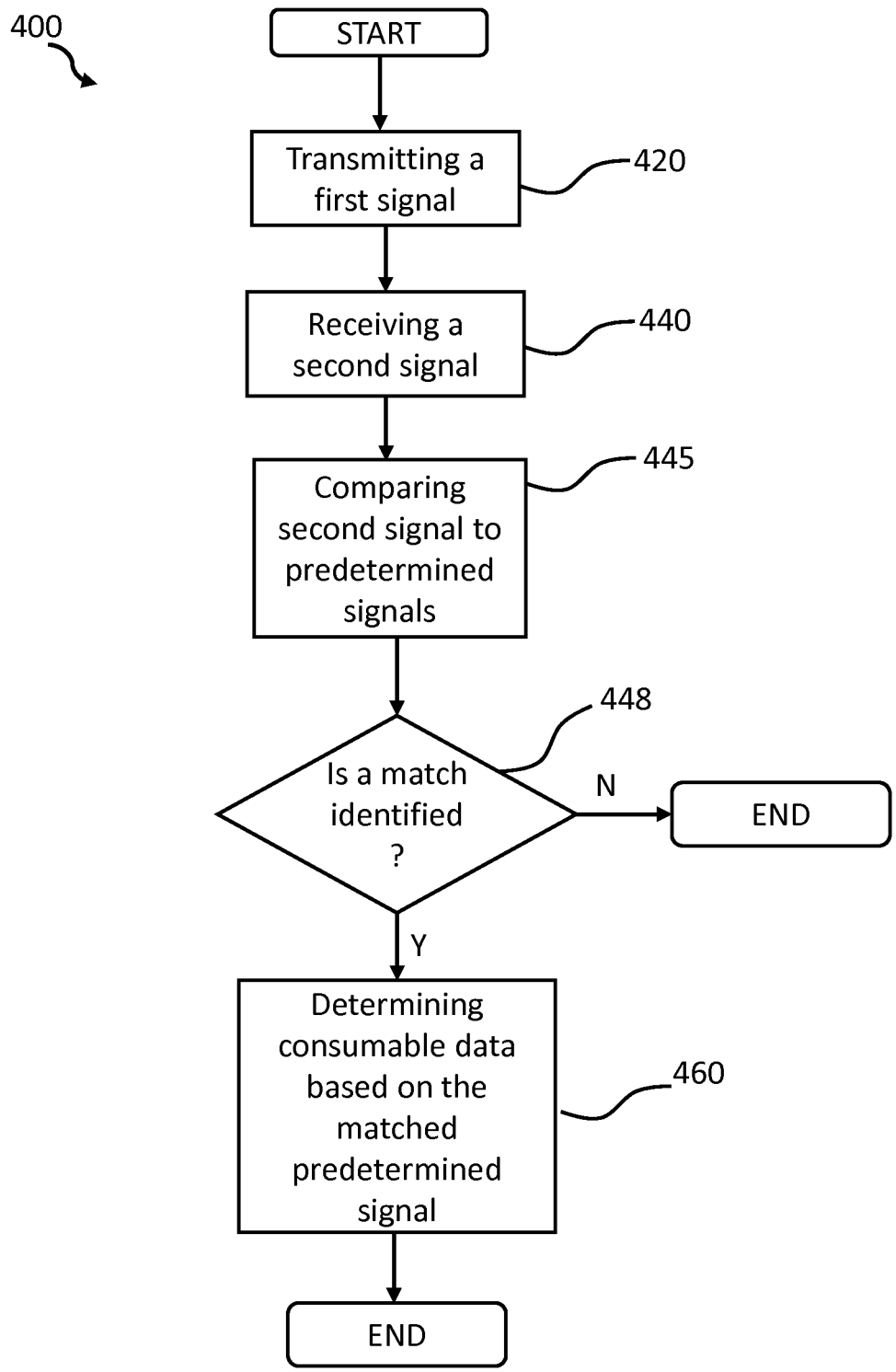
FIG. 5 shows a flow chart of a method of identifying an article of an aerosol delivery device according to an example.

Referring now to FIG. 5, a flow chart of another example method 400 of identifying a consumable in an aerosol delivery device is shown. Method 400 is similar to method 300, but rather than determining a signal alteration the second signal is used directly to determine consumable data.

Method 400 comprises a first block 420, where a first signal S1 is transmitted at least partially through a consumable 200 from a transmitter 120 to a receiver 130 spaced from the transmitter 120, where the consumable 200 has a signal altering component 220.

After the first signal is transmitted, the method 400 moves to block 440, where a second signal S2 is received at the receiver 130. The second signal S2 is the first signal S1 altered by interaction with the signal altering component 220 of the consumable 220.

Next, method 400 moves on to block 445, where the second signal S2 is compared to a plurality of predetermined signals. The plurality of predetermined signals is stored in the memory 144 of the device circuitry 140. The comparing of block 445 may compare one or more of signal strength, signal polarization, signal frequency, and signal direction of the second signal S2 to signal strength, signal polarization, signal frequency and signal direction of the plurality of predetermined signals.

Following the comparison, method 400 moves on to block 448, where a query is made as to whether a match can be identified between the second signal S2 and one of the plurality of predetermined signals. If no match is found, the method 400 ends, as shown by the no (N) branch. In some embodiments, if no match is found a feedback signal may be generated to notify a user of the aerosol delivery device 100 that the consumable 200 is not recognized. The feedback signal may generate at least one of audio, visual or haptic feedback to the user.

On the other hand, if a match is found between the second signal S2 and one of the plurality of predetermined signals, method 400 moves on to block 460, where consumable data is determined based on a matched predetermined signal, as shown by the yes (Y) branch.

Matching of the second signal S2 to a specific one of the plurality of predetermined signals is achievable because the signal altering component 220 is one of a plurality of predetermined signal altering components, where each signal altering component applies a specific alteration to the first signal S1. In this way, matching of the second signal S2 to a predetermined signal enables identification of the signal altering component 220 and subsequently, determination of consumable data of the consumable 200.

As an example, in use, the processor compares the signal power of the second signal to a plurality of predetermined signals having different signal powers. If the plurality of predetermined signals contains the signal power of the second signal as a predetermined signal power, the processor identifies a match and determines consumable data associated with the predetermined signal power. The consumable data associated with the signal power may indicate, as an example, that the flavor of the consumable is peach and the manufacture date is 1 Jan. 2018.

In some examples the methods described above may be executed by a processing system. Such examples may comprise a non-transitory computer-readable storage medium comprising a set of computer-readable instructions stored thereon, which, when executed by a processor of an aerosol delivery device, cause the device to perform any of the above-described methods, for example a method comprising: transmitting a first signal at least partially through an article from a transmitter to a receiver spaced from the transmitter; receiving a second signal at the receiver, wherein the second signal is the first signal altered by interaction with a signal altering component of the article; and determining article data from the second signal.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material to impart flavor and/or other properties to that porous solid material. As such, the liquid or oil is a constituent of the solid material in which it is impregnated.

The above embodiments are to be understood as illustrative examples of the disclosure. Further embodiments of the disclosure are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. An article for use in an aerosol delivery device comprising:
    an aerosolizable material for delivery by the aerosol delivery device; and
    a signal altering component, wherein the signal altering component is configured to alter a first signal transmitted at least partially through the article into a second signal indicative of article data, wherein the signal altering component is configured to alter at least one of:
    signal strength;
    signal polarization;
    signal frequency; or
    signal direction.

2. The article of claim 1, wherein the alteration to the first signal by the signal altering component is specific to the signal altering component.

3. The article of claim 1, wherein the signal altering component is further configured to alter signal wavelength.

4. The article of claim 1, wherein the signal altering component comprises at least one of:
    a shield;
    a conductor;
    a diffraction grating,
    a reflector, or
    a polarizer.

* * * * *